US008322198B2

(12) United States Patent
Iverson et al.

(10) Patent No.: US 8,322,198 B2
(45) Date of Patent: Dec. 4, 2012

(54) METHODS AND APPARATUS FOR DESIGNING A CEMENT COMPOSITION

(75) Inventors: Benjamin John Iverson, Duncan, OK (US); Robert Phillip Darbe, Duncan, OK (US); Rick Bradshaw, Houston, TX (US)

(73) Assignee: Halliburton Energy Services, Inc., Duncan, OK (US)

( * ) Notice: Subject to any disclaimer, the term of this patent is extended or adjusted under 35 U.S.C. 154(b) by 496 days.

(21) Appl. No.: 12/576,893

(22) Filed: Oct. 9, 2009

(65) Prior Publication Data

US 2011/0083503 A1   Apr. 14, 2011

(51) Int. Cl.
G01N 29/024 (2006.01)
(52) U.S. Cl. .............................. 73/64.53; 73/597; 73/866
(58) Field of Classification Search .................. 73/64.53, 73/597, 866
See application file for complete search history.

(56) References Cited

U.S. PATENT DOCUMENTS

| | | | |
|---|---|---|---|
| 4,377,087 A * | 3/1983 | Rodot | 73/594 |
| 5,049,288 A | 9/1991 | Brothers et al. | |
| 5,293,938 A | 3/1994 | Onan et al. | |
| 5,346,012 A | 9/1994 | Heathman et al. | |
| 5,358,047 A | 10/1994 | Himes et al. | |
| 5,412,990 A | 5/1995 | D'Angelo et al. | |
| 5,588,488 A | 12/1996 | Vijn et al. | |
| 5,688,844 A | 11/1997 | Chatterji et al. | |
| 6,715,553 B2 | 4/2004 | Reddy et al. | |
| 6,722,434 B2 | 4/2004 | Reddy et al. | |
| 6,793,730 B2 | 9/2004 | Reddy et al. | |
| 6,858,566 B1 | 2/2005 | Reddy et al. | |
| 2007/0062691 A1 | 3/2007 | Reddy et al. | |

FOREIGN PATENT DOCUMENTS

| | | |
|---|---|---|
| WO | 0155047 A2 | 8/2001 |
| WO | 0250529 A2 | 6/2002 |
| WO | 2006111559 A1 | 10/2006 |

OTHER PUBLICATIONS

Foreign communication from a related counterpart application—International Search Report and Written Opinion, PCT/GB2010/001887, Jan. 21, 2011, 9 pages.
Bamberger, Judith A., et al., "Measuring fluid and slurry density and solids concentration non-invasively," Ultrasonics, 2004, pp. 563-567, vol. 42, Elsevier B.V.
Patent application entitled "Methods of formulating a cement composition," by Ashok K. Santra, et al., filed Feb. 26, 2009 as U.S. Appl. No. 12/393,141.

* cited by examiner

*Primary Examiner* — Hezron E Williams
*Assistant Examiner* — Paul West
(74) *Attorney, Agent, or Firm* — John W. Wustenberg; Conley Rose, P.C.

(57) ABSTRACT

A method comprising preparing a baseline cement slurry comprising a cement, water, and one or more additives, placing a sample of the baseline cement slurry into a sample container having a vertical height, and measuring time of flight of energy through the sample at one or more locations along the vertical height to determine a settling property of the baseline cement slurry. A method comprising providing a settling test apparatus comprising a column having a vertical height and at least one pair of transducers positioned opposite each other with the column there between, placing a cement slurry sample within the column, and measuring time of flight of ultrasonic energy through the sample at one or more locations along the vertical height to determine a settling property of the cement slurry.

16 Claims, 4 Drawing Sheets

METHODS AND APPARATUS FOR DESIGNING A CEMENT COMPOSITION

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

1. Technical Field

This disclosure generally relates to well cementing. More specifically, the disclosure relates to a methodology for designing a cement composition and an apparatus used therein.

2. Background

Zonal isolation refers to the isolation of a subterranean formation or zone, which serves as a source of a natural resource such as gas, oil, or water, from other subterranean formations. To achieve isolation of a subterranean formation, a well bore is typically drilled down to the subterranean formation while circulating a drilling fluid through the wellbore. After the drilling is terminated, a string of pipe, e.g., casing, is run in the wellbore. Next, primary cementing is typically performed whereby a cement slurry is placed in the annulus and permitted to set into a hard mass, thereby attaching the string of pipe to the walls of the wellbore and sealing the annulus. Subsequent secondary cementing operations such as squeeze cementing may also be performed.

Generally, cement slurry design for oil field applications involves optimizing slurry density, rheology, pump time, fluid loss, settling, strength development time, gas migration during placement, and mechanical properties such as compressive strengths, tensile strength, Poisson's ratio, Young's modulus, etc. for long-term zonal isolation. These mechanical properties may be modified by the inclusion of various additives with varying densities. One challenge to the inclusion of such additives is the effect of density variations of the additives on the homogeneity of the slurry. The differing densities of additives may result in a non-uniform density distribution in the slurry. For example, higher density additives may tend to settle to the lower portion of the slurry while lower density additives tend to rise to or remain in the upper portion.

A conventional method of determining settling is performed on set cement. However, such procedure takes time since the cement has to be cured and set prior to settling measurements, which may take up to 14 days. Thus, it would be desirable to develop an improved methodology for determining settling. It would also be desirable to develop a methodology for designing a cement composition that is suitable for long-term zonal isolation in a subterranean formation.

SUMMARY

Disclosed herein is a method comprising preparing a baseline cement slurry comprising a cement, water, and one or more additives, placing a sample of the baseline cement slurry into a sample container having a vertical height, and measuring time of flight of ultrasonic energy through the sample at one or more locations along the vertical height to determine a settling property of the baseline cement slurry.

Also disclosed herein is a method comprising providing a settling test apparatus comprising a column having a vertical height and at least one pair of ultrasonic transducers positioned opposite each other with the column there between, placing a cement slurry sample within the column, and measuring time of flight of ultrasonic energy through the sample at one or more locations along the vertical height to determine a settling property of the cement slurry.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION OF THE EMBODIMENTS

Figure 1:
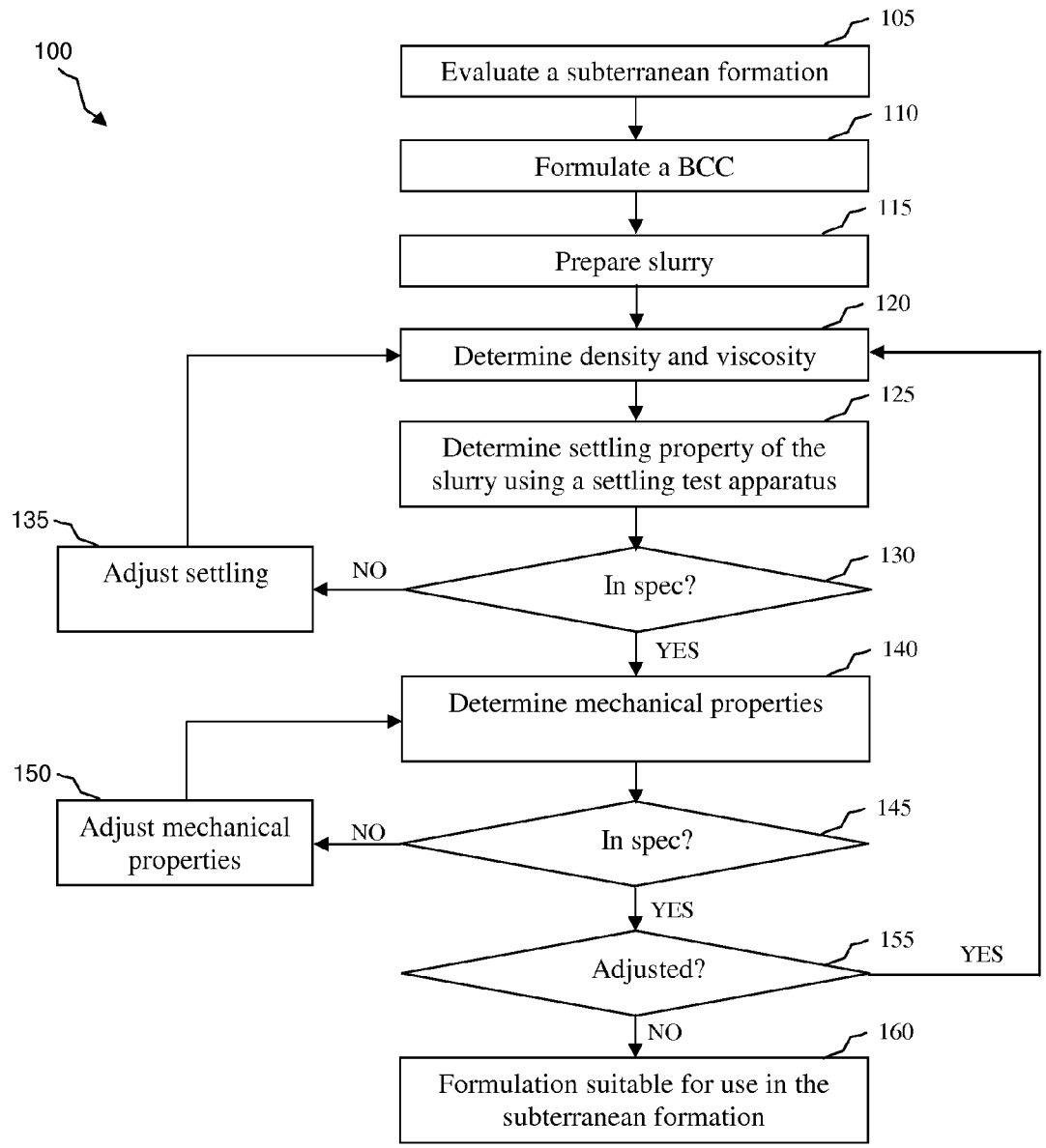
FIG. 1 is a flowchart that illustrates a method of designing a cement composition.

In the drawings and description that follow, like parts are typically marked throughout the specification and drawings with the same reference numerals, respectively. The drawing figures are not necessarily to scale. Certain features of the disclosure may be shown exaggerated in scale or in somewhat schematic form and some details of conventional elements may not be shown in the interest of clarity and conciseness.

It is to be understood that herein references made to determining the mechanical properties of a cement composition refer to determining the properties of a set cement composition. Herein an "optimized range" refers to a range of acceptable values a particular parameter may assume. The "optimized range" may be a particular range of numerical values for a parameter or may be a value relative to that of a base cement composition (BCC), as indicated. In cases where the value is relative to that of the BCC (e.g., a slurry comprised of cement, water, and optionally one or more additives) it is to be understood that the parameter being discussed was measured for the BCC in accordance with the referred to ASTM method.

Referring to FIG. 1, a flowchart illustrating a method 100 of designing a cement composition that may be suitable for cementing a subterranean formation is shown. It is to be understood that "subterranean formations" encompass both areas below exposed earth and areas below earth covered by water such as ocean or fresh water.

At block 105, the method 100 initiates with the evaluation of the subterranean formation to which the cement composition is to be introduced. The evaluation may begin with retrieval of samples of the formation and reservoir for laboratory analysis. In particular, for a wellbore, the method 100 may initiate with the gathering of information to produce a well log. Such information typically includes the characteristics of the earth formations traversed by the wellbore, and the location of subsurface reservoirs of the natural resource. Well logging is a technique for providing information to a formation evaluation professional or driller regarding the particular earth formation being drilled. The collection of information relating to conditions downhole, which commonly is referred to as "logging", can be performed by several methods. In-situ measurements of many formation properties via wellbore logging tools, such as logging-while-drilling (LWD) and wireline tools may be obtained by electromagnetic, acoustic, nuclear, or electromechanical means, for example. These logging tools enable in-situ determinations of properties such as the porosity, permeability, and lithology of the rock formations; reservoir pressure and temperature in the zones of interest; identification of the fluids present; and many other parameters. Methods of evaluating a subterranean formation and acquiring the information necessary to formulate a cement composition are known to one of ordinary skill in the art with the benefits of this disclosure.

The method 100 proceeds to block 110 where a base cement composition (BCC) is formulated. The BCC may be formulated so as to impart a targeted set of properties determined by the evaluation of the subterranean formation as previously described in block 105. Such BCCs may be formulated so as to function in support of a casing in a wellbore, to isolate a subterranean formation, or both, and shall neither exceed the fracture gradient of the formation nor allow influx of formation fluids during the cementing phase.

In an embodiment, the BCC comprises cement, water, and one or more additives. The cement may be a hydraulic cement, which includes calcium, aluminum, silicon, oxygen, and/or sulfur and sets and hardens by reaction with the water. Examples of hydraulic cements include but are not limited to Portland cements (e.g., classes A, C, G, and H Portland cements), pozzolana cements, gypsum cements, phosphate cements, high alumina content cements, silica cements, high alkalinity cements, or combinations thereof.

The BCC may include a sufficient amount of water to form a pumpable cementitious slurry. The water may be fresh water or salt water, e.g., an unsaturated aqueous salt solution or a saturated aqueous salt solution such as brine or seawater. The water may be present in an amount from about 20 to about 180 percent by weight of cement (wt. %), alternatively from about 20 to about 100 wt. %, alternatively from about 28 to about 60 wt. %.

The BCC may further comprise one or more additives that are selected to impart the baseline set of properties as necessitated by the evaluation of the subterranean formation as previously described in block 105. Examples of additives include without limitation density increasing additives such as weighting agents, density reducing additives such as glass beads, foaming and expanding additives such as gas, suspension aids, defoamers, and the like. Formulation of the BCC so as to impart the baseline set of properties as necessitated by the evaluation of the subterranean formation may be carried out by techniques known to one of ordinary skill in the art with the benefits of this disclosure.

Following the formulation of a BCC that meets the baseline set of properties as necessitated by the evaluation of the subterranean formation, the method 100 proceeds to block 115 where the BCC (i.e., slurry) is prepared by mixing cement, water, and additives. After the slurry is prepared, the method 100 proceeds to block 120 where the density and the viscosity of the slurry are determined. For example, the slurry may have a density of from about 4 lb/gallon to about 22 lb/gallon, alternatively from about 8 lb/gallon to about 20 lb/gallon, alternatively from about 12 lb/gallon to about 18 lb/gallon. The slurry may have a viscosity of from about 1 Bearden unit of Consistency (Bc) to about 100 Bc, alternatively from about 5 Bc to about 60 Bc, alternatively from about 10 Bc to about 40 Bc. In an embodiment, a measure of pumping time for the slurry is the time required to reach about 70 Bc.

Figure 2:
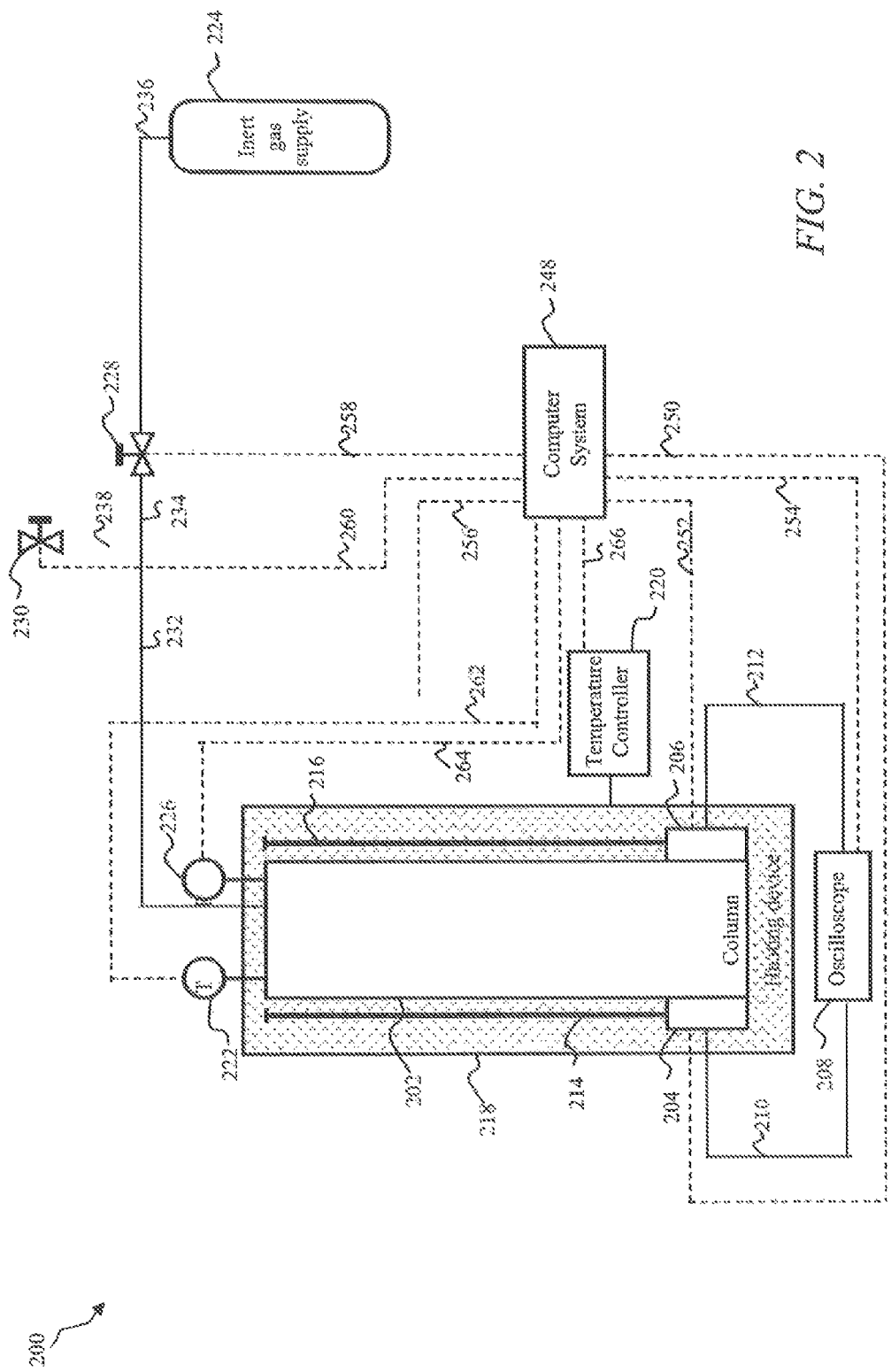
FIG. 2 is a schematic view of a settling test apparatus.
Figure 4:
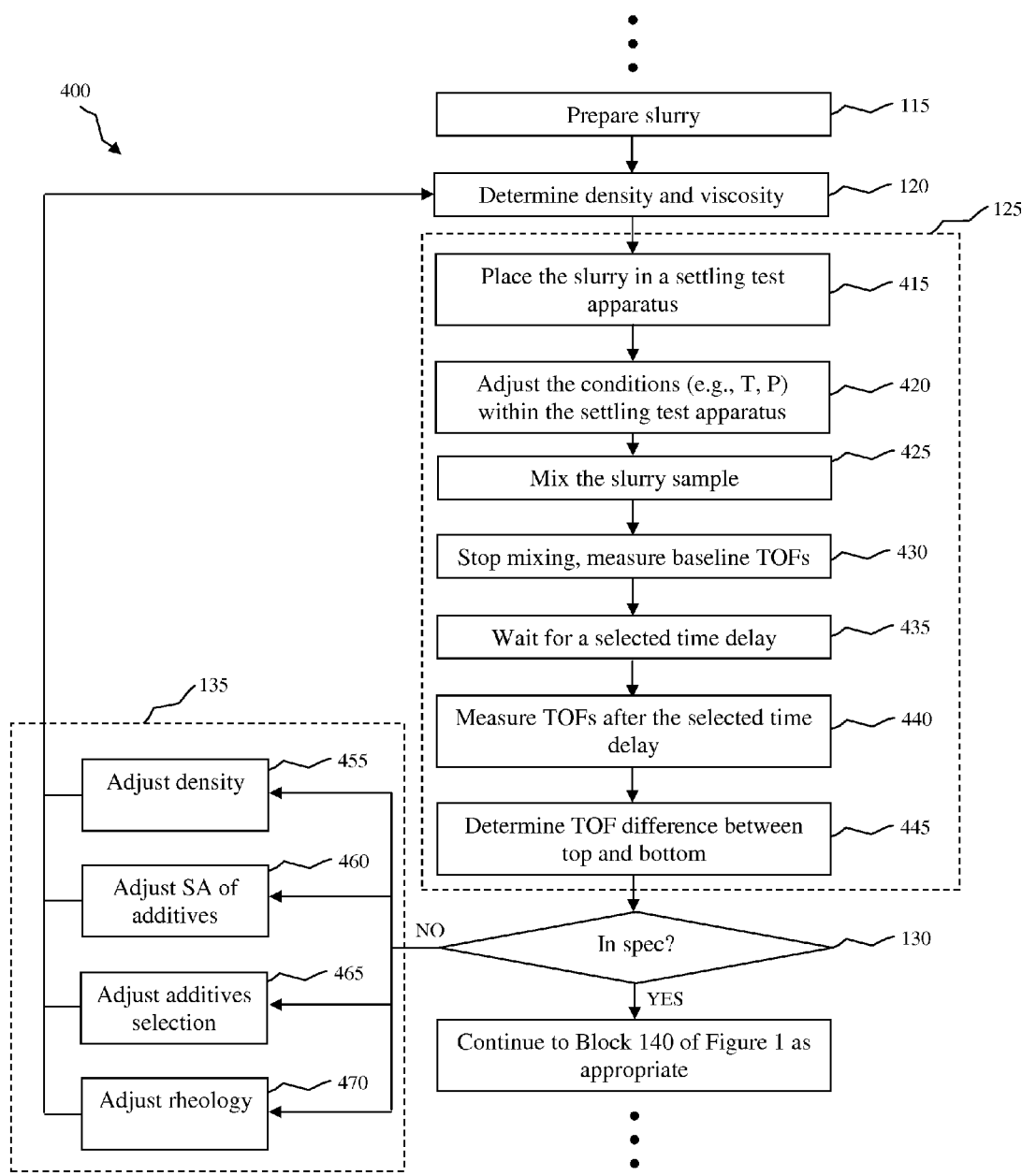
FIG. 4 is a flowchart that illustrates a method of testing settling of a cement composition using the settling test apparatus of FIG. 2.

A sample of the slurry is then placed in a settling test apparatus. The settling test apparatus (e.g., as shown in FIG. 2) and methods of using same (e.g., as shown in FIG. 4) will be described later herein. At block 125, the settling property of the slurry is determined by using the settling test apparatus prior to the slurry setting. In other words, the settling test is carried out on an unset BCC to determine its settling property using the settling test apparatus and methods as described later herein. The method 100 then proceeds to block 130 and the BCC is hereinafter referred to as a first optimized cement composition (CC-1). Without wishing to be limited by theory, a CC-1 may have a settling property in spec such that the CC-1 may be a well mixed slurry that can maintain sufficiently uniform density distribution across a vertical height over time, for example after a selected time delay or sample interval, as described infra.

At block 130, the settling property of the unset CC-1 is evaluated as to whether it falls within an optimized settling range, which is also referred to as within specification (in spec) or outside of specification (out of spec). If the settling property of the CC-1 is out of spec, the method 100 proceeds to block 135 where the settling property of the CC-1 is adjusted. The settling property, specification, and methods of adjusting same will be described in more detail later herein. After the CC-1 is adjusted, the method 100 returns to blocks 120 and 125 where the density, viscosity, and settling property of the CC-1 are again investigated. Following determination of the settling property, the method 100 again proceeds to block 130 where the CC-1 is evaluated as to whether it falls in or out of spec. If the CC-1 is out of spec, the method 100 proceeds again to block 135 wherein the settling property of the CC-1 is adjusted, as previously described. This density and viscosity determination followed by settling determination-evaluation-adjustment loop represented by blocks 120, 125, 130, and 135 continues iteratively as necessary to prepare a CC-1 having a settling property in spec.

Once the CC-1 is found to be in spec at block 130, the method 100 proceeds to block 140 where the mechanical properties such as tensile strength, compression strength, Poisson's ratio, Young's modulus, etc. of the CC-1 are determined.

Determination of these mechanical properties is known in the art with the aids of this disclosure. For example, tensile strength, which is defined as the maximum amount of tensile stress that a material can be subjected to before failure, may be determined in accordance with ASTM D3967-05. Compressive strength, which is defined as the maximum resistance of a material to an axial force, may be determined in accordance with ASTM D2938-95. Poisson's ratio, which is defined as the ratio of radial strain to axial strain, may be determined in accordance with ASTM D3148-02. Young's modulus, which indicates the elasticity of a material, may be determined in accordance with ASTM D3148-02. Additional mechanical properties that are deemed appropriate by one of ordinary skill in the art with the aids of this disclosure may also be determined.

Following determination of the mechanical properties, the method 100 proceeds to block 145 where the mechanical properties of the BCC are evaluated as to whether they are in their respective optimized ranges as determined based on the evaluation of the subterranean formation in block 105. If at least one mechanical property of the CC-1 is out of spec, the method 100 proceeds to block 150 where at least one mechanical property of the CC-1 is adjusted.

Methods of adjusting the mechanical properties of cements may be carried out using any suitable methods as known to one of ordinary skill in the art with the benefits of this disclosure. For example, the tensile and compressive strength may be adjusted by the inclusion of strength enhancing additives such as fibers, plastic, carbon, glass fibers, and the like. Various strength enhancing additives suitable for incorporation into cement slurries are described in U.S. Pat. Nos. 5,049,288, 6,793,730 and 5,358,047, each of which is incorporated by reference herein in its entirety. The Poisson's ratio may be adjusted by the inclusion of flexible, compressible beads and resilient materials such as graphite carbon, liquids, non-aqueous fluids, solids, gases, gas generating materials, and the like. Various gas generating materials suitable for incorporation into cement slurries are described in U.S. Pat. Nos. 6,715,553, 6,722,434, and 6,858,566, each of which is incorporated by reference herein in its entirety. The Young's modulus may be adjusted by the inclusion of elastomers such as polyisoprene, polybutadiene, polyisobutylene, polyethers, polyesters, etc., or rubbers such as natural rubber, styrene butadiene rubber. Various elastomers and rubber compositions suitable for incorporation into cement slurries are described in U.S. Pat. Nos. 5,688,844 and 5,293,938, each of which is incorporated by reference herein in its entirety.

Following adjustment of the mechanical properties, the method 100 returns from block 150 to block 140 where the mechanical properties are again determined as described herein previously and then to block 145 where the CC-1 is evaluated as to whether the mechanical properties fall in or out of spec. In an alternative embodiment, following adjustment of the mechanical properties, the method 100 returns from block 150 to block 130 to block 130 where the settling properties are again determined as described herein previously. Provided that the settling properties remain with specification following any adjustment to the mechanical properties, the method continues from block 130 to block 140 where the mechanical properties are again determined as described herein previously and then to block 145 where the CC-1 is evaluated as to whether the mechanical properties fall in or out of spec. Such evaluation loops may continue iteratively until the settling properties and the mechanical properties are both within specification.

In some embodiments, adjustment of one mechanical property may affect other mechanical properties. For example, increasing the tensile strength of a cement composition by adding fibers may increase the Young's modulus of the cement composition. Thus, the mechanical properties determination-evaluation-adjustment loop represented by blocks 140, 145, and 150 continues iteratively as necessary to prepare a CC-1 having all mechanical properties that are in spec within their respective optimized ranges. In some embodiments, a plurality of mechanical properties may be determined and a composition resulted therefrom may be adjusted additional times, for example, 3×, 4×, 5×, etc. to form a third optimized composition, a forth optimized composition, a fifth optimized composition, etc. Examples of methods of adjusting a plurality of mechanical properties of a cement composition are described in U.S. patent application Ser. No. 11/228,099 filed Sep. 16, 2005 and entitled "Methods of Formulating a Cement Composition," and U.S. patent application Ser. No. 12/393,141, filed on Feb. 26, 2009 and entitled "Methods of Formulating a Cement Composition", each of which is hereby incorporated by reference in its entirety. If all mechanical properties are found to be in spec within their respective optimized ranges at block 145, the method 100 proceeds to block 155.

At block 155, the method 100 determines whether the CC-1 has been adjusted at block 150. If at least one mechanical property has been adjusted, the composition of CC-1 has been altered (referred to as the adjusted CC-1), and the method 100 returns to block 120 to determine the density and viscosity of the adjusted CC-1, then to block 125 to determine the settling property of the adjusted CC-1, and subsequently to block 130 to evaluate whether the settling property remains in spec. If the settling property of the adjusted CC-1 is not in spec, the method 100 proceeds to blocks 135, 120, 125, and 130 wherein the settling property of the adjusted CC-1 is readjusted, the density and viscosity is redetermined, the settling property is redetermined and reevaluated until the settling property falls in spec, as described previously. The method 100 then proceeds to block 140 and block 145 where the mechanical properties are determined and evaluated as previously described. If at least one mechanical property of the adjusted CC-1 is not in spec, the method 100 proceeds to blocks 150, 140, and 145 wherein the mechanical properties of the adjusted CC-1 are readjusted, redetermined, and reevaluated until all of the mechanical properties fall in spec within their respective optimized ranges, as described previously. In some embodiments, determination of density and viscosity, adjustment, determination, and evaluations of the settling and/or mechanical properties of the CC-1 continue iteratively as described until the settling and the mechanical properties are in spec and no further adjustments are made to the CC-1, allowing the method 100 to proceed from block 155 to block 160. At block 160, the CC-1 is referred to as a second optimized cement composition (CC-2). Without wishing to be limited by theory, a CC-2 having mechanical properties that are in spec may have sufficient strength and sufficient resistant to deformation such that the cement composition is able to withstand the cyclic stresses experienced over the life of the structure to which the composition provides support, in addition to the advantages of a CC-1.

In various embodiments, the method 100 may conclude after block 130 to produce a CC-1 suitable for use in a wellbore to provide long term zonal isolation. Alternatively, the method 100 may conclude after block 155 to produce a CC-2 suitable for use in a wellbore to provide long term zonal isolation. Hereinafter, a BCC having at least a settling property in spec or at least one mechanical property falling within an optimized range is termed an optimized cement composition (OCC).

As deemed appropriate by one skilled in the art with the benefits of this disclosure, additional additives may be included with the OCC for adjusting the settling property and the various mechanical properties into their respective optimized ranges and/or for imparting other desired properties. Such additives may or may not simultaneously affect the settling and/or mechanical properties of the OCC. Examples of such additives include, but are not limited to, retarders, fluid loss control additives, defoamers, dispersing agents, set accelerators, formation conditioning agents, or combinations thereof.

In addition, modifications such as changes to the water-to-cement ratio and the addition of non-cementitious materials such as class F flyash may be carried out as deemed appropriate by one skilled in the art with the benefits of this disclosure to adjust the settling and/or mechanical properties (e.g., tensile strength, compressive strength, Poisson's ratio, Young's Modulus, etc.) into their respective optimized ranges. An example of class F flyash includes without limitation POZMIX A flyash, which is commercially available from Halliburton Energy Services Inc. Following inclusion of any additional additives, the settling and/or mechanical properties of the cement composition may be determined, evaluated and adjusted as disclosed herein.

The various additives described above may have various densities, sizes, shapes, surface areas, etc. that are selected such that the OCC has settling and mechanical properties that are in spec. In an embodiment, an OCC having settling and mechanical properties that are in spec is suitable for long-term zonal isolation. Alternatively, an OCC having settling property that is in spec is suitable for long-term zonal isolation.

In an embodiment, the method 100 disclosed herein may be carried out manually or may be automated using a computer in whole or part. For example, the calculations and determination of the settling property and/or mechanical properties of the disclosed cement compositions may be carried out using software and or equipment designed to evaluate and adjust the described parameters. Likewise, any or all of the determining, evaluating, and adjusting steps may be automated and/or computer controlled. For example, methods as disclosed in FIGS. 1 and 4 may be executed on a computer system of the type shown in FIG. 3 and described herein.

In an embodiment, the OCCs may be employed in well completion operations such as primary and secondary cementing operations as known to those skilled in the art. The OCC may be placed into an annulus of the wellbore and allowed to set such that it isolates the subterranean formation from a different portion of the wellbore. The OCC thus forms a barrier that prevents fluids in that subterranean formation from migrating into other subterranean formations. Within the annulus, the OCC also serves to support a conduit, e.g., casing, in the wellbore. In an embodiment, the wellbore in which the OCC is positioned belongs to a multilateral wellbore configuration. It is to be understood that a multilateral wellbore configuration includes at least two principal wellbores connected by one or more ancillary wellbores.

In secondary cementing, often referred to as squeeze cementing, the sealant composition may be strategically positioned in the wellbore to plug a void or crack in the conduit, to plug a void or crack in the hardened OCC (e.g., cement sheath) residing in the annulus, to plug a relatively small opening known as a microannulus between the hardened sealant and the conduit, and so forth. Various procedures that may be followed to use a sealant composition in a wellbore are described in U.S. Pat. Nos. 5,346,012 and 5,588,488, which are incorporated by reference herein in their entirety.

In an embodiment, the OCC is used in a wellbore that is arranged in any configuration suitable for injecting or recovering material from the wellbore, such as a steam-assisted gravity drainage (SAGD) configuration, a multilateral wellbore configuration, or a common wellbore configuration. A SAGD configuration comprises two independent wellbores with horizontal sections arranged one above the other. The upper wellbore is used primarily to convey steam downhole, and the lower wellbore is used primarily to produce oil. The wells are positioned close enough together to allow for heat flux from one to the other. Oil in a reservoir adjacent to the upper wellbore becomes less viscous in response to being heated by the steam such that gravity pulls the oil down to the lower wellbore where it can be produced. In an embodiment, the OCCs of this disclosure provide set cement compositions that are thermally stable when subjected to high temperature environments.

Referring now to FIG. 2, a schematic view of an embodiment of a settling test apparatus 200 for determining the settling property discussed in FIG. 1 is shown. The settling test apparatus 200 may simulate downhole conditions and may be used to investigate particle (e.g., additives) settling over time of a slurry (e.g., an unset cement composition). The disclosed settling test apparatus 200 and methods of using same may also offer capability for a user to improve overall efficiency in formulating a cement composition based on the needs of a subterranean formation.

As depicted, the settling test apparatus 200 comprises a vessel or a receptacle for holding a sample, which is referred to generally herein as a column 202. In an embodiment, the column 202 may have any suitable shape, for example, cylindrical, cuboid, etc. In an embodiment (e.g., having a cylindrical shape), the column 202 may have smoothed interior edges or corners to aid in the elimination of void during mixing so that a well blended slurry may be achieved Generally, sharp edges or corners may lead to areas of dead-zones wherein the slurry may have pockets of different densities. The column 202 may have any suitable size and configuration. In an embodiment, the column 202 is a laboratory size apparatus. In such an embodiment, the column 202 may be equal to or less than 5 feet, or equal to or less than 4 feet, or equal to or less than 3 feet. Alternatively, the column 202 may be smaller or larger than the laboratory size apparatus. The column 202 may be constructed from any suitable material, for example, metal, stainless steel, composite, glass, plastics, etc.

In an embodiment, the column 202 may be a metal container such as a tin container. The tin container may have a cuboid shape having smoothed interior edges and corners with a height of 8 inches, a width of 4 inches, and a length of 2 inches.

The settling test apparatus 200 further comprises ultrasonic transducers 204 and 206 positioned facing each other with the column 202 therebetween. As depicted, ultrasonic transducers 204 and 206 are positioned at the same height and are movable vertically by moving them upward or downward along vertical axis 214 and 216, respectively. In that way, the location of ultrasonic transducers 204 and 206 may be adjustable for settling property measurements at any desirable height along the vertical axis 214 and 216. For example, ultrasonic transducers 204 and 206 may be moved as a pair upward toward the upper portion of the column 202, alternatively they may be moved as a pair downward toward the lower portion of the column 202. In alternative embodiments, there may be more than two ultrasonic transducers (e.g., 4, 6, 8, 10, etc.) in a settling test apparatus placed fixed and/or movable vertically along the height of a column. In those embodiments, the settling property may be measured simultaneously at any point with or without moving the ultrasonic transducers upward or downward. For example, a settling test apparatus may comprise six ultrasonic transducers, wherein two ultrasonic transducers are placed facing each other at the upper portion, two ultrasonic transducers are placed facing each other at the lower portion, and the remaining two ultrasonic transducers are placed facing each other at the middle portion of that settling test apparatus. In an alternative embodiment, a single ultrasonic transducer (or other odd number such as 3 or 5) is employed, wherein at least one transducer produces a signal (e.g., sound wave) and receives a reflected signal. For example a signal is transmitted through the wall of a sample container and passes through the sample. At least a portion of the signal is reflected back through the sample and container wall and is received by the same transducer that produced the signal. Appropriate adjustments could be made to the signal processing described herein, for example to take into account the approximate doubling of the time of flight given the reflected nature of the signal.

Ultrasonic transducers 204 and 206 are devices that can both generate and receive high frequency sound waves. Thus, when two ultrasonic transducers 204 and 206 are placed across from each other, one of the ultrasonic transducers (e.g., ultrasonic transducer 204 or ultrasonic transducer 206) may send electrical energy (e.g., signal voltages) and turn the electrical energy into ultrasonic sound waves, typically above 20,000 hertz, and the other ultrasonic transducer (e.g., ultrasonic transducer 206 or ultrasonic transducer 204) may receive the ultrasonic sound waves and turn them back into signal voltages. In alternative embodiments, other devices for sending and receiving energy signals (e.g., transceivers) may be employed in place of or in addition to the ultrasonic transducers. In various embodiments, the energy signals may comprise acoustic signals (normal acoustical or sound waves), gamma rays, x-rays, neutrons, or combinations thereof. In embodiments, such energy signals are sourced by transmitter-receiver pairs of transducers.

In an embodiment, the ultrasonic transducers 204 and 206 are coupled to a display device such as an oscilloscope 208 via lines 210 and 212, respectively. Oscilloscope 208 is a device that allows both the sent and received signal voltages to be viewed so that the transient time between the two signals may be determined. In other words, the time of flight (TOF) between the sending of high frequency sound waves and the receiving of high frequency sound waves by ultrasonic transducers 204 and 206 may be determined using the oscilloscope 208. TOF is defined as the amount of time for ultrasonic sound waves to travel over a known distance, which is the width of column 202 between ultrasonic transducers 204 and 206. An example of an oscilloscope 208 is Tektronix TDS 1000, which is a commercially available oscilloscope from Tektronix. In alternative embodiments, other devices may be employed to determine or measure time of flight, for example signal processing clock (e.g., microchip or integrated circuit device).

The settling test apparatus 200 may be further equipped with a temperature controller 220 that controls the temperature in the settling test apparatus 200 using a heating device 218. Examples of suitable heating devices include without limitation heating bands, jackets, coils, heating elements, or combinations thereof, which may fully or partially surround or penetrate the settling test apparatus 200. The temperature controller 220 may be used to heat the slurry sample within the column 202 to a desired temperature, for example to a bottomhole static temperature (BHST) to simulate downhole conditions. A temperature sensor 222 may be disposed within the column 202 to measure the temperature therein.

The settling test apparatus 200 may be coupled to an inert gas supply 224 via lines 232, 234, and 236 for pressurizing the column 202 to a desired pressure, for example to a downhole pressure to simulate downhole conditions. In alternative embodiments, the settling test apparatus 200 may be pressurized by alternative methods such as a syringe pump or a controlled air-over-water pump, alone or in combination with a pressure relief valve. Additionally or alternatively to gas, other pressurizing mediums may be employed such as water or other fluids/liquids. The inert gas supply 224 may be any suitable pressurized inert gas such as nitrogen, argon, etc. A pressure sensor 226 may be disposed within the column 202 to measure the pressure therein. A pressure regulator 228 disposed between the column 202 and the inert gas supply 224 may be used to regulate the flow of pressurized inert gas from the inert gas supply 224 into the column 202. A pressure relief valve 230 disposed between the column 202 and the pressure regulator 228 may be used to release any pressure buildup within the column 202 caused by an equipment failure or a process upset via lines 232, 238, and 240.

The settling test apparatus 200 may further comprise a mixer 242 rotatably disposed within the column 202 for mixing or agitating a slurry sample therein. The mixer 242 may be coupled to a shaft 244, which in turn may be coupled to a driver unit 246 for rotating the mixer 242. The driver unit 246 may be any known means for rotating mixer 242 such as without limitation engines, mixers, motors, etc. In an embodiment, the settling test apparatus 200 mixes the slurry at a desired speed to achieve a well-blended slurry having a uniform density. As depicted, the mixer 242 and the shaft 244 are mounted from the top of the column 202 and may be movable, for example, they may be pulled upward and held so that they do not obstruct the area between ultrasonic transducers prior to settling determination, which is described later herein. In alternative embodiments, however, a mixer and a shaft may be placed strategically so that they do not obstruct the area between ultrasonic transducers, for example, the mixer and the shaft may be mounted from the side of a column. Alternatively, a mixer and a shaft may be removable, for example, the mixer and the shaft may be used for mixing a slurry within a column and removed after the slurry is well mixed.

The settling test apparatus 200 may alternately comprise a vibrator or other device, method, or means for accelerating the settling action of the slurry. In an embodiment, the vibrator comprises a vibrating pad or base upon which all or a portion of the settling test apparatus 200 is placed (e.g., column 202). This induced vibration may occur internal to the test apparatus 200 or external to the apparatus. Even though vibration is typically avoided to reduce the settling action, it may be induced purposefully to accelerate the settling action in the interest of decreasing the overall testing time.

The settling test apparatus 200 may alternately comprise a pump-around or cyclic flow loop or other device, method, or means for simulating the settling under dynamic conditions (e.g., under fluid flow conditions). In an embodiment, the flow loop is in fluid communication with column 202. The flow loop may comprise one or more outlets for removing slurry from the apparatus, one or more inlets for receiving the slurry back into the apparatus, associated flow conduits connecting the inlet and outlet, and one or more pumps disposed within the flow conduits. Alternately, the slurry may be pumped through and discarded rather than cycled into and out of the apparatus.

In an embodiment, the settling test apparatus 200 and associated methods may also be used in a real time pumping situation to measure settling in cement installations, for example wellbore cementing operations. In various embodiments, the settling test apparatus 200 may be installed on the pumping equipment, or could be installed on a tool to be deployed down hole. The ultrasonic method may be installed in a flow path of a real time cement job at a remote job site, such as a well site. For example, a sample could be pulled from a cement mixer, placed in the settling test apparatus 200 in real time, and optionally returned to the cement mixer or optionally discarded. Alternatively, a sampling stream could be pulled from a cement mixer, circulated though the settling test apparatus 200 in real time (e.g., an apparatus having flow loop as described above), and optionally returned to the cement mixer or optionally discarded. The properties of the cement (e.g., a wellbore cement) may thereby be monitored and adjusted in real time to achieve desired settling properties while performing the cementing job (e.g., primary and/or secondary cementing in a wellbore).

Figure 3:
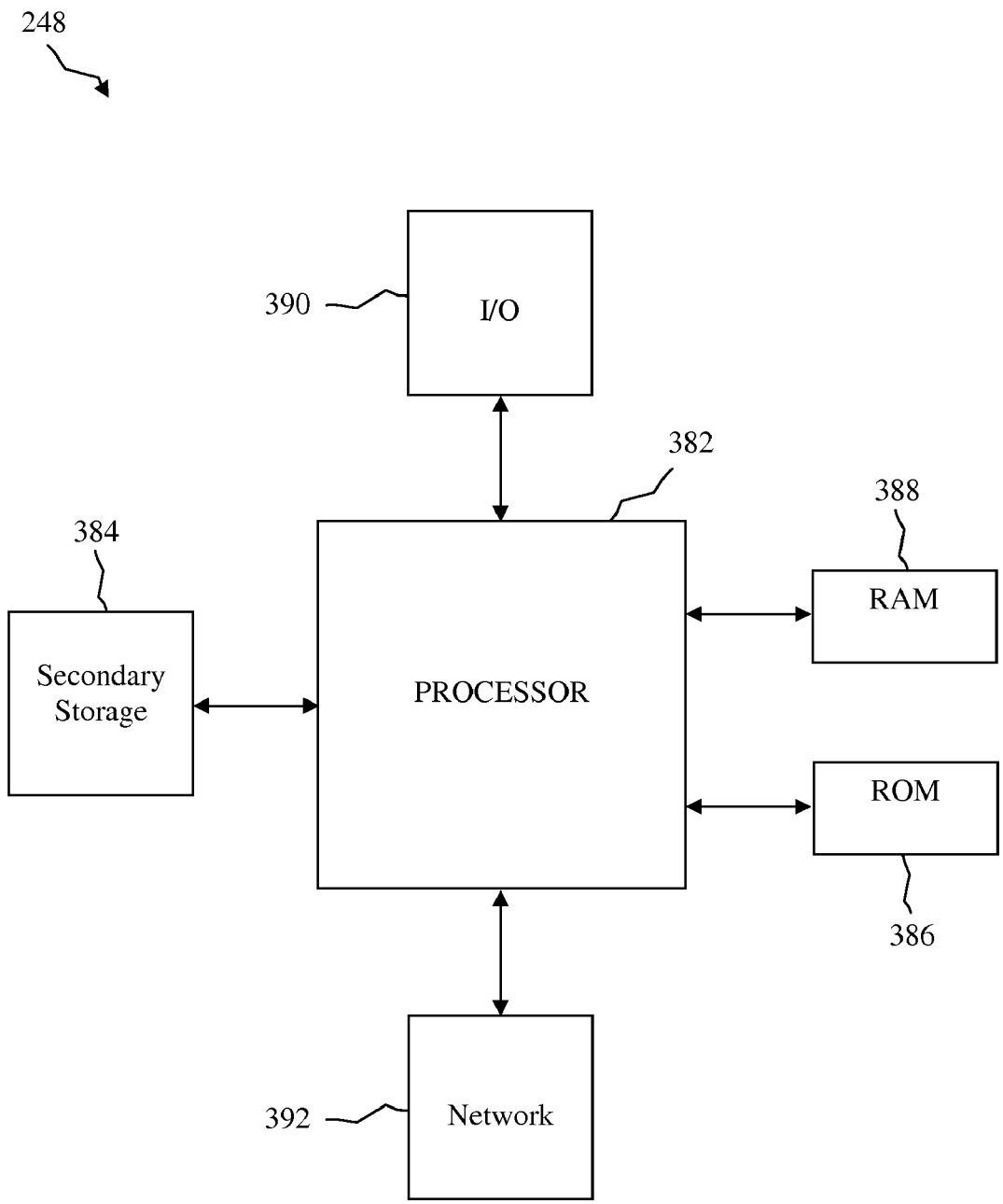
FIG. 3 illustrates a computer system suitable for implementing the several embodiments of the disclosure.

The settling test apparatus 200 may further comprise a computer system 248. Ultrasonic transducers 204 and 206, oscilloscope 208, driver unit 246, pressure regulator 228, pressure relief valve 230, temperature sensor 222, pressure sensor 226, and temperature controller 220 may be coupled to the computer system 248 via lines 250, 252, 254, 256, 258, 260, 262, 264, and 266, respectively. The computer system 248 and processing controls and/or methodology (e.g., all or a portion of the method shown in FIG. 4) may be implemented on a computer having sufficient processing power, memory resources, and network throughput capability to handle the necessary workload placed upon it. FIG. 3 illustrates a computer system 248 suitable for implementing one or more embodiments disclosed herein. The computer system 248 includes a processor 382 (which may be referred to as a central processor unit or CPU) that is in communication with memory devices including secondary storage 384, read only memory (ROM) 386, random access memory (RAM) 388, input/output (I/O) 390 devices, and network connectivity devices 392. The processor may be implemented as one or more CPU chips.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage. The RAM 388 is used to store volatile data and perhaps to store instructions. Access to both ROM 386 and RAM 388 is typically faster than to secondary storage 384.

I/O 390 devices may include printers, video monitors, liquid crystal displays (LCDs), touch screen displays, keyboards, keypads, switches, dials, mice, track balls, voice recognizers, card readers, paper tape readers, or other well-known input and output devices. The network connectivity devices 392 may take the form of modems, modem banks, ethernet cards, universal serial bus (USB) interface cards, serial interfaces, token ring cards, fiber distributed data interface (FDDI) cards, wireless local area network (WLAN) cards, radio transceiver cards such as code division multiple access (CDMA) and/or global system for mobile communications (GSM) radio transceiver cards, and/or worldwide interoperability for microwave access (WiMAX) radio transceiver cards, WiFi, Bluetooth, and other well-known network devices. These network connectivity 392 devices may enable the processor 382 to communicate with an Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embodied in the carrier wave generated by the network connectivity 392 devices may propagate in or on the surface of electrical conductors, in coaxial cables, in waveguides, in optical media, for example optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, referred to herein as the transmission medium, may be generated according to several methods well known to one skilled in the art.

The processor 382 executes instructions, codes, computer programs, scripts which it accesses from hard disk, floppy disk, optical disk (these various disk based systems may all be considered secondary storage 384), ROM 386, RAM 388, or the network connectivity devices 392.

The network connectivity devices 392 of the computer system 248 are capable of facilitating communications between the processor 382 and components of the settling test apparatus 200 including ultrasonic transducers 204 and 206, oscilloscope 208, driver unit 246, pressure regulator 228, pressure relief valve 230, temperature sensor 222, pressure sensor 226, and temperature controller 220. In an embodiment, the network connectivity devices 392 may be wired devices such as Ethernet cards, USB interface cards, etc. and the communications between the processor 382 and the components of the settling test apparatus 200 may be wired network communications. Alternatively, the network connectivity devices 392 may be wireless devices such as WiFi, Bluetooth, etc. and the communications between the processor 382 and the components of the settling test apparatus 200 may be wireless network communications.

Sensors (e.g., ultrasonic transducers 204 and 206, temperature sensor 222, pressure sensor 226, etc.) may be coupled to the computer system 248 such that data obtained from such sensors may be stored and/or used by the computer system 248. In an embodiment, the TOFs of a slurry across a vertical height of column 202 may be measured at the beginning of an experiment (at time zero, $t_0$) and at the end of the experiment (at time $t_{end}$) after a selected time delay that may be selected by a user. In alternative embodiments, the settling property (e.g., TOFs) of a slurry within the column 202 may be monitored continuously during an experiment and data sampling may be collected periodically throughout the experiment at every sample interval (e.g., at time $t_1$, $t_2$, $t_3$, etc.), for example, every second, every minute, every hour, etc.

The computer system 248 is capable of receiving internal data and/or external data and generating and delivering signals to oscilloscope 208, driver unit 246, pressure regulator 228, pressure relief valve 230, and temperature controller 220. For example, the computer system 248 may receive automated and/or manual instructions from a user input, and may send signals to oscilloscope 208, driver unit 246, pressure regulator 228, pressure relief valve 230, and temperature controller 220 based on internal calculations, programming, and/or data received from sensors. Thus, the computer system 248 may be coupled to oscilloscope 208 for displaying the high frequency sound waves from ultrasonic transducers 204 and 206 and the TOFs across same. The computer system 248 may be coupled to driver unit 246 for rotating mixer 242 and shaft 244. The computer system 248 may also be coupled to temperature controller 220 and temperature sensor 222 to control the temperature of the slurry within the column 202 based upon feedback from temperature sensor 222. The computer system 248 may also be coupled to pressure regulator 228 and pressure sensor 226 to control the pressure within the column 202 by adjusting the amount of inert gas entering the column 202 from inert gas supply 224 based upon feedback from pressure sensor 226. The computer system 248 may also be coupled to pressure relief valve 230 and pressure sensor 226 to monitor any equipment failure or process upset causing pressure buildup within the column 202 and release such pressure buildup by opening pressure relief valve 230. As such, the computer system 248 may be capable of affecting various functions of the settling test apparatus 200 including oscilloscope 208, temperature controller 220, temperature within the column 202, pressure regulator 228, pressure relief valve 230, pressure within the column 202, driver unit 246, mixer 242 speed, and the like. In alternative embodiments, however, it is also envisioned that an oscilloscope, a temperature controller, a driver unit, a pressure regulator, and a pressure relief valve may be adjusted manually by controls external to a computer system.

Referring now to FIG. 4, an embodiment of a method 400 of testing a settling property using the settling test apparatus 200 of FIG. 2 is shown. This method 400 describes blocks 125 and 135 of method 100 of FIG. 1 in greater detail. The method 400 initiates at block 115 of FIG. 1 where a slurry (i.e., BCC) is prepared. The slurry (i.e., BCC) may be prepared by mixing cement with water and additives. The method 400 proceeds to block 120 of FIG. 1 where the density and viscosity of the slurry is determined. After determination of density and viscosity, the method 400 proceeds to block 125 further comprising blocks 415-445. At block 415, where the slurry is placed in the column 202 of the settling test apparatus 200 of FIG. 2. At block 420, the conditions of the settling test apparatus 200 is adjusted. For example, the heating device 218 may be turned on if not already on, the temperature controller 220 may be adjusted to a selected temperature to simulate downhole temperature, and the temperature within the settling test apparatus 200 may be monitored with temperature sensor 222 to achieve the selected temperature. The pressure regulator 228 and the pressure relief valve 230 may be closed off at first. Next, inert gas from inert gas supply 224 may be introduced into the column 202 by opening pressure regulator 228 until a selected pressure (e.g., a downhole pressure) is reached. The pressure within the column 202 may be monitored with pressure sensor 226. The pressure regulator 228 may be closed off when the pressure within the settling test apparatus 200 reaches the selected pressure.

Next, the method 400 proceeds to block 425 where the slurry inside the column 202 is mixed for example by turning on driver unit 246 to a selected speed, which turns the shaft 244 and the mixer 242. Stirring the slurry may simulate the placing of slurry downhole and also provides a baseline for a well mixed slurry. At block 430, after the slurry is well mixed, the stirring may be stopped by turning off driver unit 246. Shaft 244 and mixer 242 may be pulled upward so that they don't obstruct the area between ultrasonic transducers 204 and 206. Oscilloscope 208 may be turned on. The TOF at the top of slurry may be measured by moving ultrasonic transducers 204 and 206 upward along vertical axis 214 and 216 so that ultrasonic transducers 204 and 206 are level with the top of slurry inside the column 202. Next, the TOF at the bottom of slurry may be measured by moving ultrasonic transducers 204 and 206 downward along vertical axis 214 and 216 so that ultrasonic transducers 204 and 206 are positioned at the bottom of column 202. TOF measurements at the top and at the bottom of slurry may be carried out simultaneously or almost simultaneously while the slurry is well mixed. Herein, the TOFs at the top and at the bottom of slurry may be substantially similar and provides a baseline of a well mixed slurry at time zero. In an embodiment, a baseline well mixed slurry at time zero may have a TOF difference between the top and the bottom of less than about 15%, alternatively less than about 10%, alternatively less than about 5, 4, 3, 2, or 1%, alternatively about zero, i.e. TOF at top and bottom are about equal.

Next, the method 400 proceeds to block 435 where the slurry is allowed to settle by waiting for a selected time delay or sample interval, which may be selected by a user. At block 440, after the selected time delay or sample interval, the TOFs at the top and at the bottom of the slurry were remeasured by moving both ultrasonic transducers 204 and 206 so that they are level with the top and bottom of the slurry, respectively, as described herein previously.

At block 445, the method 400 determines the difference in TOF between the top and the bottom of the slurry after the selected time delay or sample interval. In an embodiment, the sample interval is from about 1 minute to about 24 hours, alternatively from about 10 minutes to about 4 hours, alternatively from about 30 minutes to about 60 minutes. As settling occurs over time, heavier particles (e.g., additives, etc.) settle toward the lower portion of column 202 and lighter particles settle toward the upper portion of column 202. This results in the density at the upper portion of the slurry decreasing while the density at the lower portion of the slurry increases.

Without wishing to be limited by theory, ultrasonic transducers 204 and 206 measure the relative density of the slurry as a function of height (i.e., height of column 202) and time (i.e., the selected time delay or sample interval). The speed of sound through a given medium (i.e., slurry) is proportional to the density of the medium. As particles settle over time in the slurry, the density uniformity of the slurry begins to change. While the net flux of particle migration from the top and the bottom of the slurry remains unchanged, particle redistribution at the top and the bottom caused by settling will result in a change in particle concentration in the slurry from the top to the bottom over time. This change in particle concentration in the slurry causes non-uniform density distribution from the top to the bottom. Thus, the speed of sound through the top and the bottom of the slurry changes over time as settling occurs.

Since sound travels faster in solid than in liquid, the speed of sound at the upper portion decreases as heavy particles settle over time, thereby decreasing the TOF at the upper portion of the slurry. On the contrary, the speed of sound at the lower portion increases, thereby increasing the TOF at the lower portion of the slurry over time.

The method 400 continues to block 130 of FIG. 1 where the method 400 determines whether the difference in TOFs after the selected time delay or sample interval is in spec. The difference in TOFs after the selected time delay or sample interval indicates the variation in density of a slurry over a vertical height and time, which further indicates particle settling in the slurry. The specification for the difference in TOFs after the selected time delay or sample interval may be defined by a user. For example, a user may correlate the difference in TOFs of the slurry with density variations determined conventionally on a set cement, and thereby define acceptable or unacceptable differences (e.g., percentage differences) in TOFs for the slurry.

In an embodiment, a slurry may be tested on two different methods, for example a first sample may be tested using the methods described herein while a second sample may be tested using a conventional method, such as a BP Settling method. Both samples may be prepared under similar conditions and mixed for example using mixers. At time zero, the mixers may be removed on both samples. Next, on the first sample, TOFs may be measured across a vertical height and, after a selected time delay or sample interval, the TOFs may be remeasured. Meanwhile, the second sample may be allowed to settle for the selected time delay or sample interval and then allowed to set. The set second sample may be cut into sections and the density of each section may be measured. The density variation between the sections measured on the second sample may be correlated to the difference in TOFs across a vertical height over the selected time delay or sample interval.

Herein, a slurry having a settling property in spec may be represented by a difference in TOF between the top and the bottom of the column 202 over a sample interval (e.g., after a selected time delay or sample interval) of equal to or less than 1, 2, 3, 4, 5, 10, 15, 20, 25, or 30%. In other embodiments, the settling property may be considered in spec where the settling property (i.e., the difference in TOFs after the selected time delay or sample interval) is equal to or less than 1, 2, 3, 4, 5, 10, 15, 20, 25, or 30% in comparison to a baseline settling property for a given slurry. If the settling property (i.e., the difference in TOFs after the selected time delay or sample interval) is out of spec, the method 400 proceeds to block 130 where the slurry sample is modified.

There are a variety of ways to modify the slurry. As depicted, slurry modifications are represented by block 135 further comprising blocks 455-470. At block 455, the slurry may be modified by adjusting the density of such slurry. Heavy weight additives such as weighting agents may be added to the slurry to increase slurry densities while light weight additives may be added to decrease slurry densities. Generally, heavy weight additives refer to additives with a specific gravity of from about 6.0 to 1.0, alternatively from about 5.2 to 2.2, alternatively from about 3.18 to 2.5. Specific gravity is defined as the ratio of the density of a given material to the density of water, when both are at the same temperature. The higher the specific gravity, the denser the material, thus the increased tendency of the material to sink or settle toward the bottom part of the slurry. Examples of suitable heavy weight additives include without limitation barite, hematite, hausmannite, calcium carbonate, siderite, ilmenite, or combinations thereof. Examples of commercially available heavy weight additives include without limitation BAROID 41 and SWEEP-WATE, which are barite, HI DENSE #3 weighting agent and HI DENSE #4 weighting agent, which are hematite, MICROMAX weighting agent, which is hausmannite, each of which is commercially available from Halliburton Energy Services, Inc.

On the other hand, light weight additives generally refer to additives with a specific gravity of from about 1.5 to 0.001, alternatively from about 1.0 to 0.01, alternatively from about 0.5 to 0.1. Examples of light weight additives include without limitation elastomers or thermoplastic elastomers (TPEs). Without limitation, examples of TPEs include dienes such as butadiene, isoprene and hexadiene, and/or monoolefins such as ethylene, butenes, and 1-hexene. The TPEs may be polymers comprising aromatic hydrocarbon monomers (e.g., styrene, alpha-methyl styrene, vinyltoluene, etc.) and aliphatic dienes. The TPEs may be crosslinked or partially crosslinked such as for example styrene butadiene block copolymer, styrene butadiene styrene (SBS) block copolymer, styrene butadiene random (SBR) copolymer, and the like. The light weight additives may also include polyolefin grafted with polar monomers such as maleic anhydride, sulfonic acid or sulfonate groups and the like. Examples of commercially available light weight additives include without limitation WELLLIFE 665 available from Halliburton Energy Services, Inc., and FINAPRENE 411, FINAPRENE 435, FINAPRENE 401, and FINACLEAR thermoplastic elastomers, which are SBS elastomers commercially available from Total Petrochemical USA, Inc., and KRATON elastomers which are also SBS elastomers commercially available from Kraton Polymers.

These heavy weight and light weight additives may have a particle size of from about 1 micron to about 3000 microns, alternatively from about 20 microns to about 2000 microns, alternatively from about 60 microns to about 1000 microns, and a surface area of from about 3.1 E-6 mm$^2$ to about 28.3 mm$^2$, alternatively from about 1.3 E-3 mm$^2$ to about 12.6 mm$^2$, alternatively from about 1.1 E-2 mm$^2$ to about 3.1 mm$^2$.

Alternatively, at block 460, slurry modification may be carried out by adjusting the surface area of the additives described herein previously to reduce or prevent settling. Reducing the surface area of particles, for example by selecting smaller diameter particles or by mixing smaller and larger diameter particles may lead to an increased in suspension ability, which in turn reduces settling.

Alternatively, at block 465, the type of additives used may be removed and/or replaced with other types that have better suspension properties and therefore less likely to settle.

Alternatively, at block 470, the rheology of the BCC may be adjusted. Rheology refers to the deformation and flow of matter under the influence of an applied stress. The rheology of the BCC may be adjusted for example by modifying the viscosity of the BCC. Any suitable viscosifiers that can increase the viscosity of the BCC may be added to the slurry. Viscosifiers are well known in the art with the aids of this disclosure. Examples of viscosifiers include without limitation sodium montmorillonite such as AQUALGEL viscosifier, biopolymer zanthan gum such as BARAZAN viscosifier, fatty acid such as TEMPERUS viscosifier, each of which is commercially available from Halliburton Energy Services, Inc. In various embodiments, the rheology of the BCC may be adjusted in one or more iterations of the method, may be held constant in one or more iterations of the method, or combinations thereof.

In an embodiment, slurry modification may be carried out by adjusting density (block 455), adjusting the surface area of additive (block 460), adjusting the selection of additives (block 465), adjusting the rheology of the BCC (block 470), or combinations thereof. Alternatively, slurry modification may be carried out by adjusting density (block 455), adjusting the surface area of additive (block 460), adjusting the selection of additives (block 465), and adjusting the rheology of the BCC (block 470). Alternatively, slurry modification may be carried out by adjusting density (block 455), adjusting the surface area of additive (block 460), and adjusting the selection of additives (block 465). Alternatively, slurry modification may be carried out by adjusting density (block 455) and adjusting the surface area of additive (block 460). Alternatively, slurry modification may be carried out by adjusting density (block 455) and adjusting the selection of additives (block 465). Alternatively, slurry modification may be carried out by adjusting the surface area of additive (block 460) and adjusting the selection of additives (block 465). Alternatively, slurry modification may be carried out by adjusting density (block 455) and adjusting the rheology of the BCC (block 470). Alternatively, slurry modification may be carried out by adjusting density (block 455). Alternatively, slurry modification may be carried out by adjusting the surface area of additive (block 460). Alternatively, slurry modification may be carried out by adjusting the selection of additives (block 465). Alternatively, slurry modification may be carried out by adjusting the rheology of the BCC (block 470).

Following modification of the slurry sample, the method 400 proceeds to blocks 120, 125 (415-445), and 130, as described previously herein. If the difference in the TOFs between the top and the bottom of the slurry after the selected time delay or sample interval are in spec, the method 400 continues to 140 of FIG. 1 as appropriate.

The method 400 offers a non-invasive technique for measuring particle setting in a cement composition while the cement composition is in a slurry form prior to setting. This technique allows for in-situ measurements so that as soon as the density variations develop in the slurry, such density variations may be identified. The method may also provide additional information about the slurry such as yield strength, Poison's ratio, Young's modulus, as well as a better understanding of impedance of the fluid. The method also provides for much quicker evaluation as to whether the cement displays acceptable or unacceptable settling characteristics.

In an embodiment, all or a portion of the steps set forth in FIG. 1 and/or FIG. 4 may be carried out at a job site, for example a wellbore site such as a drilling/completion unit or platform. Also, in one or more embodiments, all or a portion of the steps set forth in FIG. 1 and/or FIG. 4 may be carried out in real time or about real time at a job site, for example a wellbore site such as a drilling/completion unit or platform. For example, method steps as represented by one or more of blocks 115, 120, 125, 130, 135, and combinations thereof may be carried out at a job site (e.g., a wellbore site such as a drilling/completion unit or platform), and further may be carried out in real time or about real time to provide information regarding settling characteristics of the cement being used at the job site (e.g., placed downhole in primary and/or secondary cementing services). Such information can be used to adjust the parameters of the job and/or cement as needed to meet the job objectives.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Example 1

Proof of concept experiments were carried out to demonstrate a correlation between TOF measurements and density variations across a vertical height over time. First, the density of water was measured using a settling apparatus similar to FIG. 2 and compared to the known value of water density of 1,000 kg/m$^3$.

The speed of sound through a material may be used to quantify the density of a material using Equation 1.

$$\rho = \frac{Z_m}{c} \quad \text{Equation 1}$$

The column, which was a tin container having a width of 0.075 m, was filled with water. The temperature and pressure within the tin container were kept at ambient conditions. Next, TOFs were measured using ultrasonic transducers and an oscilloscope across the width of the tin container at the top and at the bottom of water. The ultrasonic transducers were made in house and the oscilloscope used was Tektronix TDS 1000, which was commercially available from Tektronix.

The speed of sound through water was determined using the TOF measurement and the width of the tin container. The TOFs at the top and at the bottom were similar at $4.9 \times 10^{-6}$ s and the TOF difference between the top and the bottom was 0, which indicated that the density of water was uniform from the top to the bottom. The acoustical impedance of water is a known value of 1.4833 10$^6$ m·kg/s·m$^3$/Rayls. The density of water was then calculated at 978 kg/m3, which was comparable to the known density of water of 1,000 kg/m$^3$. Differences between the calculated and the known density of water may be due to the sides of the tin container that were not accounted for in the calculation.

Next, the settling of silica flour in water was investigated using the settling test apparatus. A mixture comprising silica flour and water was prepared and the density of a well mixed mixture was measured at 1,500 kg/m$^3$. The mixture was then placed in the tin container and maintained at a well mixed state using a mixer. The mixer was then removed and while the mixture was still in a well mixed state, the TOFs were measured at the top and the bottom of the mixture, which were 47 μs and 45 μs respectively. The results indicated that silica flour started settling in water immediately, as shown by a TOF difference of 2 μs. In this experiment, the time between removal of the mixer and measurement of TOFs was enough to allow silica flour to settle in water, as observed by measurable TOF changes between the top and the bottom of the mixture.

The mixture was allowed to settle for 30 minutes. After 30 minutes, TOFs were remeasured at the top and the bottom of the mixture at 49 μs and 44 μs respectively and a TOF difference of 5 μs. The mixture was allowed to settle again for another 30 minutes for a total of 60 minutes from the time the first TOF measurements were taken. Afterwards, TOFs were remeasured again at the top and the bottom of the mixture at 49 μs and 43 μs respectively and a TOF difference of 6 μs. The results of the TOF measurements for water and silica flour mixture are also tabulated in Table 1.

TABLE 1

| Time delay (minutes) | TOF top (μs) | TOF bottom (μs) | TOF difference (μs) |
| --- | --- | --- | --- |
| 0 | 47 | 45 | 2 |
| 30 | 49 | 44 | 5 |
| 60 | 49 | 43 | 6 |

The results showed that the TOFs at the top of the mixture increased over time while the TOFs at the bottom of the mixture decreased over time. Without wishing to be limited by theory, the changes in the density of the mixture over time suggested that silica flour settled down toward the bottom of the tin container thereby increasing the density at the bottom of the mixture and decreasing the density at the top of the mixture. In general, sound travels faster through solids than through liquids because the molecules in solids are packed closer than the molecules in liquids. The closer the molecules, the easier for those molecules to collide with one another to carry the sound, which results in faster speed of sound. Thus, the TOF at the bottom of the mixture decreased over time since the speed of sound was faster with increasing density. On the contrary, the TOF at the top of the mixture increased over time since the speed of sound was slower with decreasing density. In addition, as silica flour settled in water over time, the density variation between the top and the bottom increased as observed by the increased in TOF difference over time.

While embodiments of the disclosure have been shown and described, modifications thereof can be made by one skilled in the art without departing from the spirit and teachings of the disclosure. The embodiments described herein are exemplary only, and are not intended to be limiting. Many variations and modifications of the disclosure disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$, and an upper limit, $R_U$, is disclosed, any number falling within the range is specifically disclosed. In particular, the following numbers within the range are specifically disclosed: $R=R_L+Fk*(R_U-R_L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference herein is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method comprising:
preparing a baseline cement slurry comprising a cement, water, and one or more additives;
placing a sample of the baseline cement slurry into a sample container having a vertical height; and
measuring time of flight of energy through the sample at one or more locations along the vertical height to determine a settling property of the baseline cement slurry;
wherein the time of flight is measured at a plurality of locations spaced vertically apart along the vertical height of the sample container, wherein a difference between time of flight measured at the plurality of locations spaced vertically apart indicates settling within the slurry.

2. The method of claim 1 wherein measuring time of flight of energy comprises:
measuring first time of flight at a first time;
measuring second time of flight at a later, second time; and
comparing the first time of flight to the second time of flight,
wherein a difference between first time of flight and the second time of flight indicates settling within the slurry.

3. The method of claim 2 wherein the time of flight is measured at a plurality of times and the plurality of locations spaced vertically apart along the vertical height of the sample container.

4. The method of claim 3 wherein a difference between time of flight measured at the plurality of times, the plurality of locations spaced vertically apart, or both indicates settling with the slurry.

5. The method of claim 1 wherein the time of flight is measured simultaneously at the plurality of locations spaced vertically apart along the vertical height of the sample container.

6. The method of claim 1 further comprising comparing the settling property of the baseline cement slurry to a reference settling value.

7. A method comprising:
preparing a baseline cement slurry comprising a cement, water, and one or more additives;
placing a sample of the baseline cement slurry into a sample container having a vertical height;
measuring time of flight of energy through the sample at one or more locations along the vertical height to determine a settling property of the baseline cement slurry; and
comparing the settling property of the baseline cement slurry to a reference settling value, wherein the reference value is determined by correlating time of flight measurements for a cement slurry to additional settling measurements taken at corresponding measurement locations after the slurry has set.

8. A method comprising:
preparing a baseline cement composition comprising a cement, water, and one or more additives;
placing a sample of the baseline cement composition into a sample container having a vertical height;
measuring time of flight of energy through the sample at one or more locations along the vertical height to determine a settling property of the baseline cement composition;
comparing the settling property of the baseline cement composition to a reference settling value; and
where the baseline cement composition does not comply with the reference settling value, adjusting the baseline cement composition based upon the settling property to produce an adjusted baseline cement composition.

9. The method of claim 8 wherein adjusting the baseline cement composition comprises altering the density of the composition, the surface area of one or more additives in the composition, the selection of one or more additives in the composition, the amount of one or more additives in the composition, the rheology of the composition, or combinations thereof.

10. The method of claim 8 further comprising iteratively measuring time of flight of energy through the sample at one or more locations along the vertical height to determine the settling property of the adjusted cement slurry; comparing the settling property of the adjusted cement composition to the reference settling value; and adjusting the cement composition based upon the settling property until the cement composition complies with the reference settling value, thereby providing a firstly optimized cement composition.

11. The method of claim 10 further comprising determining at least one mechanical property of the firstly optimized cement composition, comparing the mechanical property of the firstly optimized cement composition to a reference mechanical value; and where the firstly optimized cement composition does not comply with the reference mechanical value, adjusting the firstly optimized cement composition based upon the mechanical property.

12. The method of claim 11 further comprising iteratively determining at least one mechanical property of the firstly optimized cement composition, comparing the mechanical property of the firstly optimized cement composition to a reference mechanical value; and adjusting the firstly optimized cement composition based upon the mechanical property until the cement composition complies with the reference settling value, thereby providing a secondly optimized cement composition.

13. The method of claim 12 further comprising placing the secondly optimized cement composition down a wellbore.

14. The method of claim 10 further comprising placing the firstly optimized cement composition down a wellbore.

15. A method comprising:
providing a settling test apparatus comprising a column having a vertical height and at least one pair of transducers positioned opposite each other with the column there between;
placing a cement slurry sample within the column;
measuring time of flight of energy through the sample with the pair of transducers at one or more locations along the vertical height to determine a settling property of the sample; and
comparing the settling property of the sample to a reference settling value, wherein the reference value is determined by correlating time of flight measurements for a cement slurry to additional settling measurements taken at corresponding measurement locations after the slurry has set.

16. A method comprising:
providing a settling test apparatus comprising a column having a vertical height and at least one pair of transducers positioned opposite each other with the column there between;
placing a cement slurry sample within the column;
measuring time of flight of energy through the sample with the pair of transducers at one or more locations along the vertical height to determine a settling property of the sample;
comparing the settling property of the sample to a reference settling value; and
where the sample does not comply with the reference settling value, adjusting the sample based upon the settling property to produce an adjusted cement slurry sample.

* * * * *